United States Patent
Wessjohann et al.

(10) Patent No.: US 10,435,673 B2
(45) Date of Patent: Oct. 8, 2019

(54) METHOD FOR THE BIOTECHNOLOGICAL PRODUCTION OF FLAVONOIDS

(71) Applicant: Symrise AG, Holzminden (DE)

(72) Inventors: Ludger Wessjohann, Halle (DE); Anne-Kathrin Bauer, Halle (DE); Jakob Ley, Holzminden (DE); Torsten Geissler, Einbeck (DE); Katrin Geissler, Einbeck (DE)

(73) Assignee: SYMRISE AG, Holzminden (DE)

( * ) Notice: Subject to any disclaimer, the term of this patent is extended or adjusted under 35 U.S.C. 154(b) by 87 days.

(21) Appl. No.: 15/514,120

(22) PCT Filed: Sep. 27, 2015

(86) PCT No.: PCT/EP2015/072189
§ 371 (c)(1),
(2) Date: Mar. 24, 2017

(87) PCT Pub. No.: WO2016/050656
PCT Pub. Date: Apr. 7, 2016

(65) Prior Publication Data
US 2018/0135029 A1 May 17, 2018

(30) Foreign Application Priority Data
Oct. 3, 2014 (EP) .................................. 14187583

(51) Int. Cl.
| C12P 17/06 | (2006.01) |
| C12N 9/10 | (2006.01) |
| C12N 9/02 | (2006.01) |
| C12N 15/64 | (2006.01) |

(52) U.S. Cl.
CPC ......... *C12N 9/1007* (2013.01); *C12N 9/0071* (2013.01); *C12N 15/64* (2013.01); *C12P 17/06* (2013.01); *C12Y 114/14001* (2013.01); *C12Y 201/01* (2013.01)

(58) Field of Classification Search
None
See application file for complete search history.

(56) References Cited

FOREIGN PATENT DOCUMENTS

| WO | 2005/084305 A1 | 9/2005 |
| WO | 2005/115377 A1 | 12/2005 |

OTHER PUBLICATIONS

Lee at al, "Biotransformation of Flavonoids with O-Methyltransferase from Bacillus cereus," J. Microbiol. Biotechnol. (2008), 16(7), pp. 1090-1096.
Kitamura et al, "Production of Hydroxlated Flavonoids with Cytochrome P450 BM3 Variant F87V and Their Antioxidative Activities," Biosci. Biotechnol. Biochem. 77(6), pp. 1340-1343 (2013).
Wessjohann et al, "Alkylating enzymes," Current Opinion in Chemical Biology 2013, 17:229-235.
Kasai et al, "Enzymatic properties of cytochrome P450 catalyzing 3'-hydroxylation of naringenin from the white-rot fungus Phanerochaete chrysosporium," Biochemical and Biophysical Research Communications 387 (2009), pp. 103-108.
Kabumoto et al, "Directed Evolution of the Actinomycete Cytochrome P450 MoxA (CYP105) for Enhanced Activity," Biosci. Biotechnol. Biochem. 73(9), pp. 1922-1927 (2009).
European Search Report dated May 19, 2015 in corresponding European Application No. 14187583.1.
First Examination Report dated Dec. 22, 2017 in corresponding European Application No. 14187583.1.
Bhuiya, M., et al., "Engineering Monolignol 4-O-Methyltransferases to Modulate Lignin Biosynthesis," Journal of Biological Chemistry, vol. 285, No. 1, pp. 277-285 (Jan. 1, 2010).
Ravichandran, K., et al., "Crystal Structure of Hemoprotein Domain of P450BM-3, a Prototype for Microsomal P450's," Science, vol. 261, pp. 731-736 (Aug. 6, 1993).
Wils, C., et al., "A Single Amino Acid Determines Position Specificity of an *Arabidopsis thaliana* CCoAOMT-like O-methyltransferase," FEBS Letters, vol. 587, pp. 683-689 (Feb. 14, 2013—on-line).

*Primary Examiner* — Jennifer E Graser
(74) *Attorney, Agent, or Firm* — Polsinelli PC

(57) ABSTRACT

A method is proposed for producing flavonoids, comprising the steps: (a) providing of a transgenic microorganism, containing (i) a first nucleic acid section (A), comprising or consisting of a gene coding for a CYP450 oxidase, (ii) a second nucleic acid section (B), comprising or consisting of a gene coding for a plant O-methyltransferase, and (b) adding of one or more flavanones to the transgenic microorganism, (c) the conversion of the substrate flavanones by the transgenic microorganism to the corresponding flavonoids, and optionally (d) isolating and purifying of the final products.

6 Claims, 8 Drawing Sheets
Specification includes a Sequence Listing.

Plasmid pSYM_BM3 with CYP450 oxidase gene

Plasmid pSYM_PFOMT gene coding for O-methyltransferase

Plasmid pSYM_AtCOMT gene coding for cation-independent O-methyltransferase

Biocatalytic transformation from naringenin to eriodictyol

Biocatalytic transformation from eriodictyol to homoeriodictyol

Fermentative transformation from naringenin to homoeriodictyol

Fermentative transformation from eriodictyol to homoeriodictyol

Fermentative transformation from naringenin to eriodictyol

Isolation of CYP450 oxidase BM3

Isolation of O-methyltransferase PfOMT

Isolation of O-methyltransferase AtCOMT

Comparison of product formation of various variants of BM3

METHOD FOR THE BIOTECHNOLOGICAL PRODUCTION OF FLAVONOIDS

FIELD OF THE INVENTION

The invention is in the field of biotechnology and relates to a process in which flavanone is converted to the corresponding flavonoids without requiring any intermediate chemical steps, a corresponding microorganism, a vector, and a host cell.

STATE OF THE ART

Flavonoids such as, for example, homoeriodictyol, eriodictyol (EP 1258200 B1) and hesperetin (EP 1998636 B1) represent important flavouring and aroma substances. These substances are usually produced by an aldol reaction of free or partially methylated acetophloroglucinol with free or partially methlylated protocatechualdehyde. Although the processes have been established on an industrial scale, they exhibit significant disadvantages: during the course of reaction it is necessary to provide the phenolic functions with protective groups which need to be removed at a later point in time. As a result, the syntheses become multi-stage, i.e. technically complex and obviously also costly.

The subject-matter of WO 2005 115377 A1 is a food composition, comprising flavonoids and tocotrienol, wherein the flavonoids may represent naringenin, hesperidin, nobiletin or tangeretin.

However, it is particularly disadvantageous that these are chemical methods of production, i.e. for regulatory reasons the food additives, flavouring substances and aromas so produced may not be designated as natural. However, a designation as natural or nature-identical is crucial for many consumers when making their purchase decision; it is, therefore, obvious that there is a particular demand for corresponding flavonoids that are allowed to bear this designation.

A way out might be the production of flavonoids from plant-based materials, for example, by extraction from *Eriodictyon* spp. However, these processes are time-consuming and costly, they are partly based on wild harvesting of the plants, they depend on the season, are solvent and process-intensive, and are, therefore, also unsuitable for wide commercial use.

It was therefore the object of the present invention to provide a process for the production of flavonoids, particularly of eriodictyol, hesperetin, sterubin and/or homoeriodictyol, which is free from the disadvantages described above. A particular focus was intended to be on the fact that the flavonoids can be provided within short reaction times and in high yields, wherein the process should be free of chemical reaction steps so that the reaction products can subsequently be designated as natural or nature-identical.

DESCRIPTION OF THE INVENTION

Figure 1:
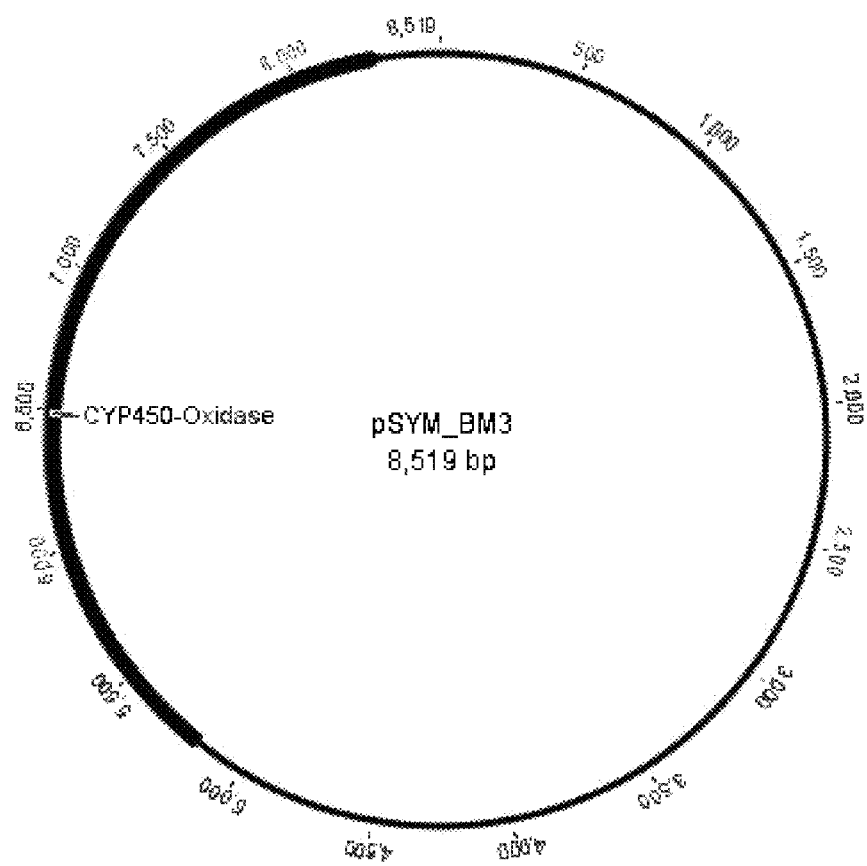
FIG. 1 depicts a plasmid pSYM BM3 with CYP450 oxidase gene.
Figure 2:
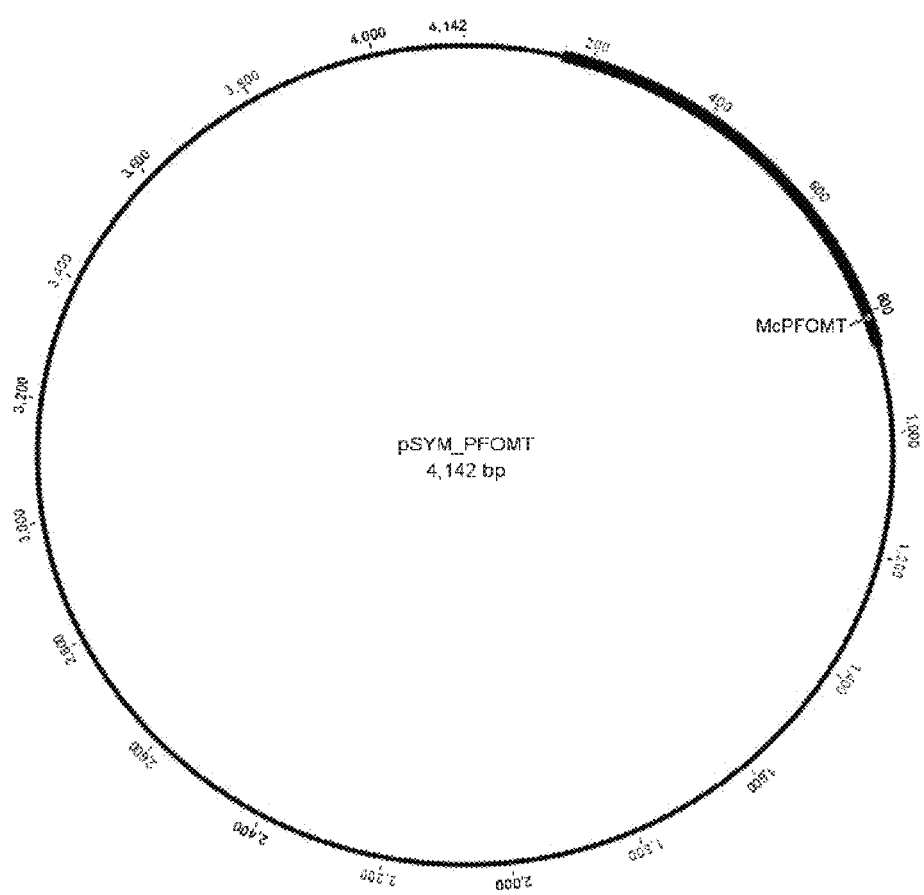
FIG. 2 depicts a plasmid pSYM PFOMT gene coding for O-methyltransferase.
Figure 3:
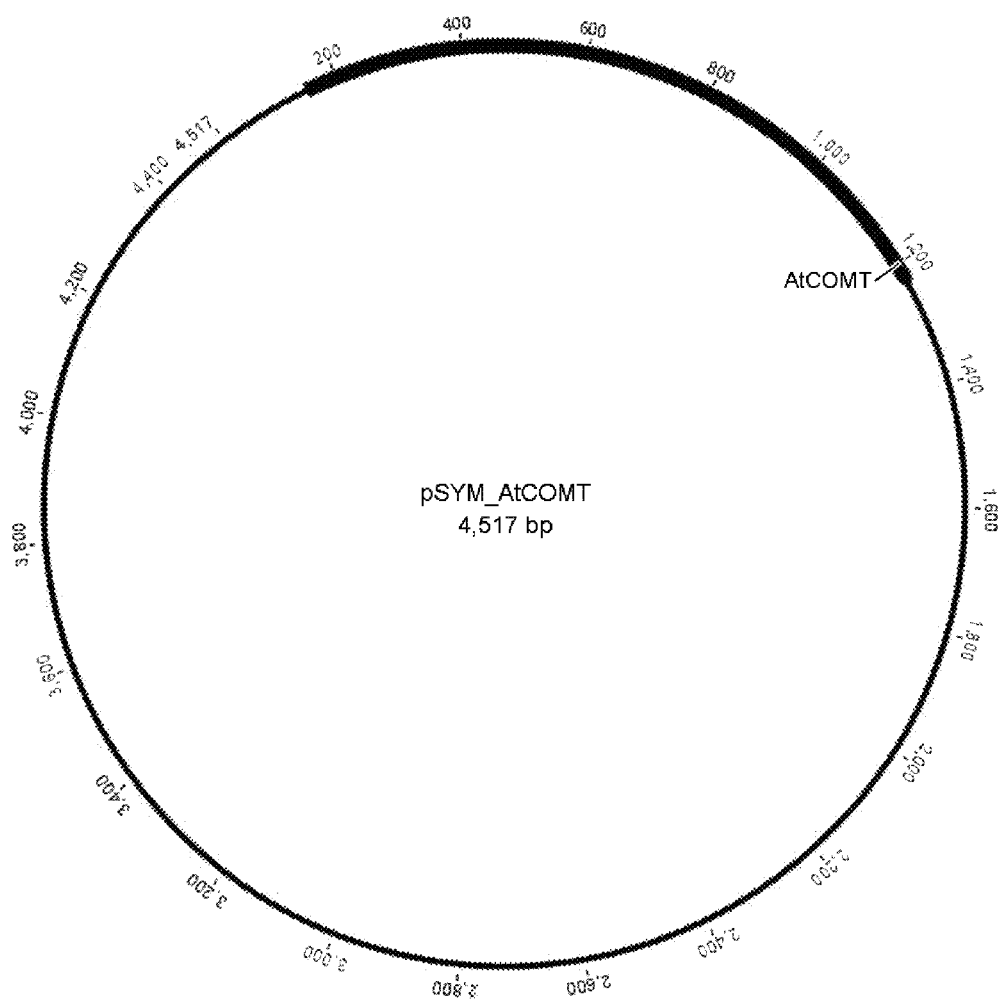
FIG. 3 depicts a plasmid pSYM AtCOMT gene coding for cation-independent O-methyltransferase.
Figure 4:
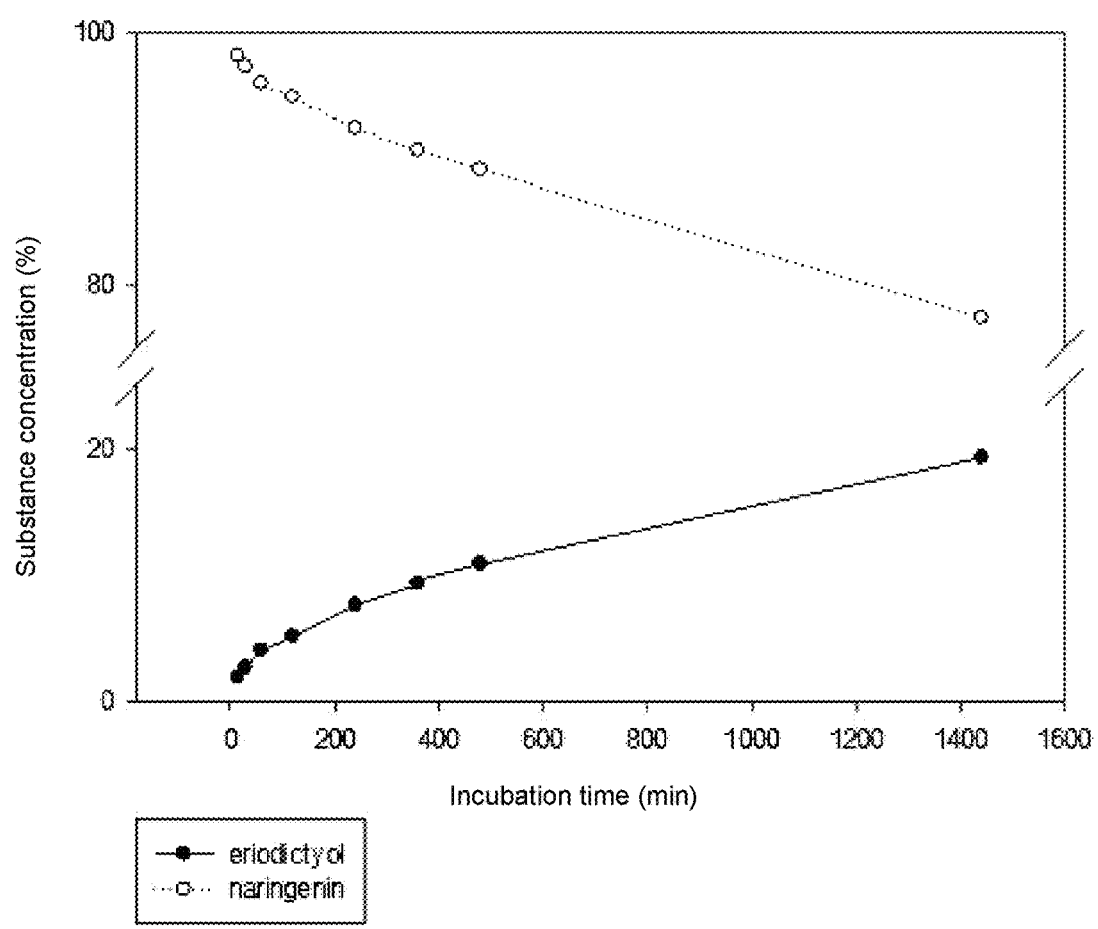
FIG. 4 shows the biocatalytic transformation from naringenin to eriodictyol.
Figure 5:
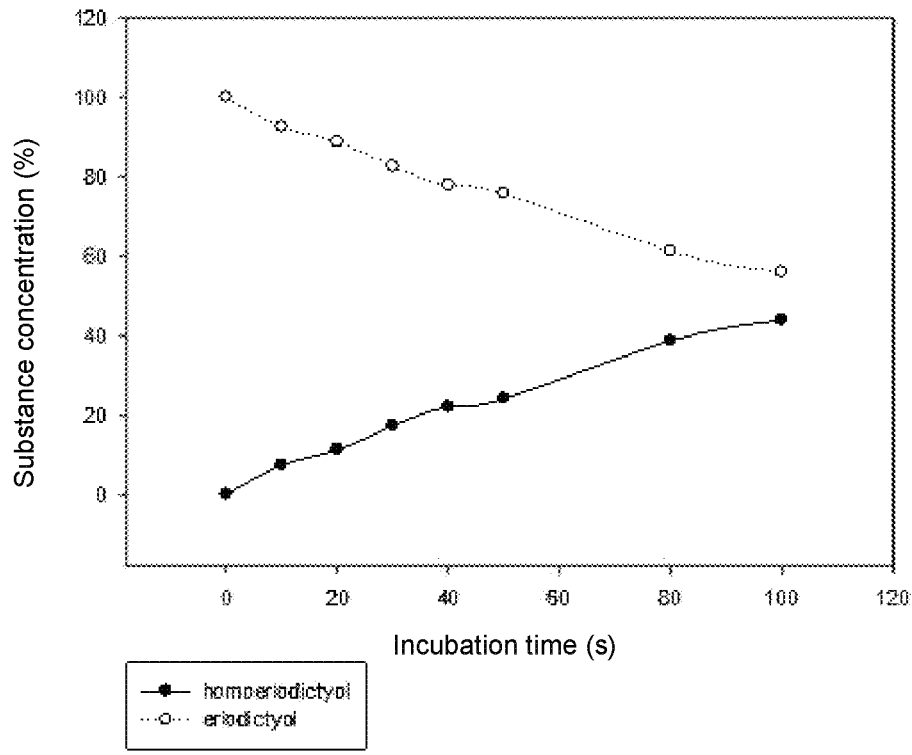
FIG. 5 shows the biocatalytic transformation from eriodictyol to homoeriodictyol.
Figure 6:
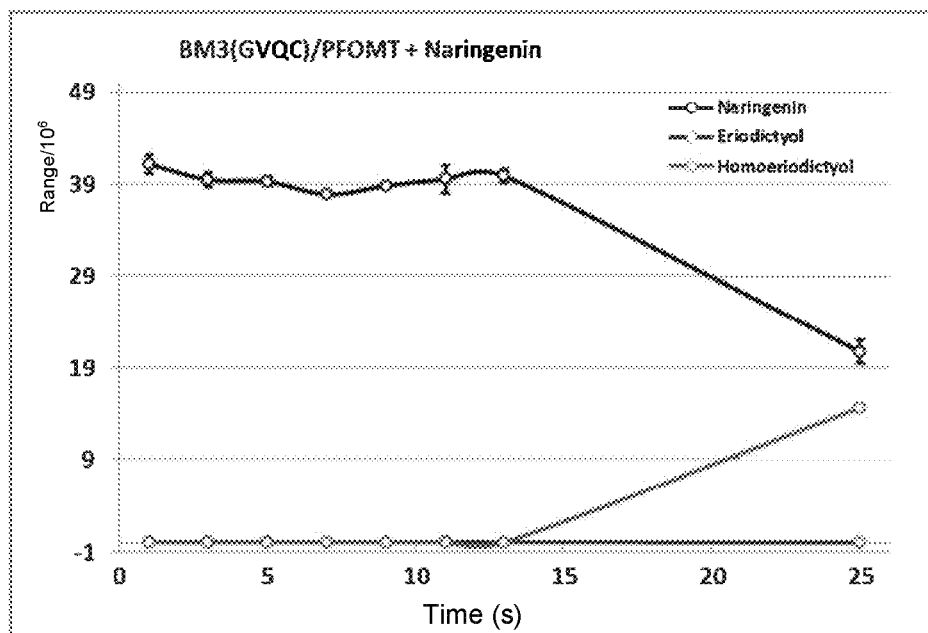
FIG. 6 shows the fermentative transformation from naringenin to homoeriodictyol.
Figure 7:
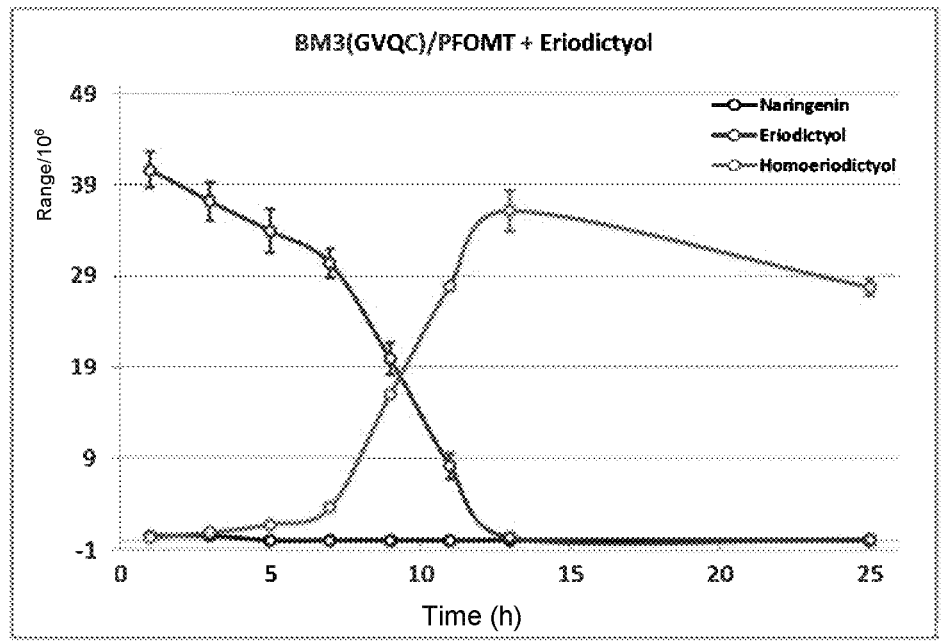
FIG. 7 shows the fermentative transformation from eriodictyol to homoeriodictyol.
Figure 8:
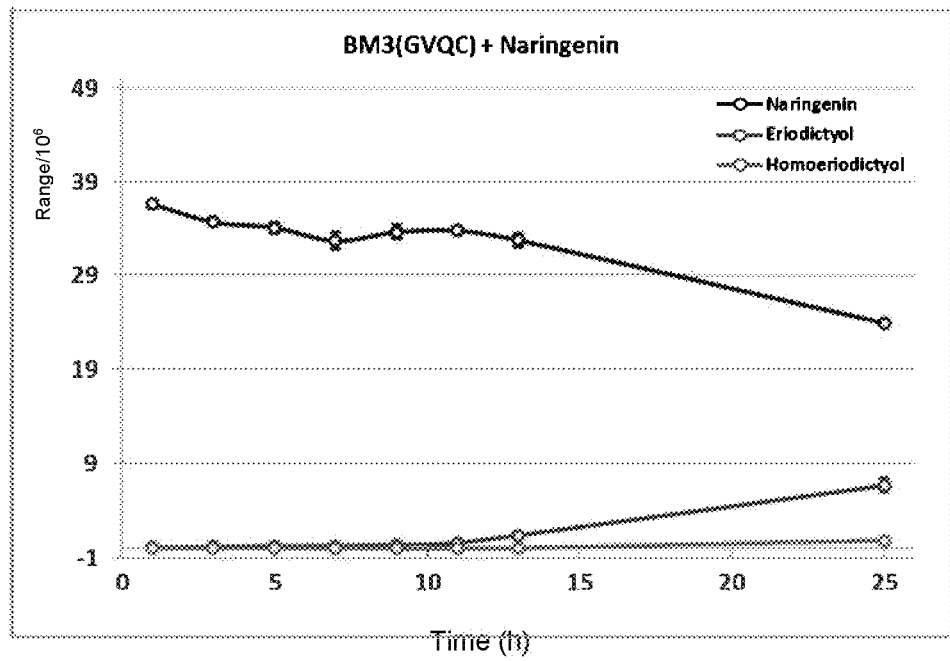
FIG. 8 shows the fermentative transformation from naringenin to eriodictyol.
Figure 9:
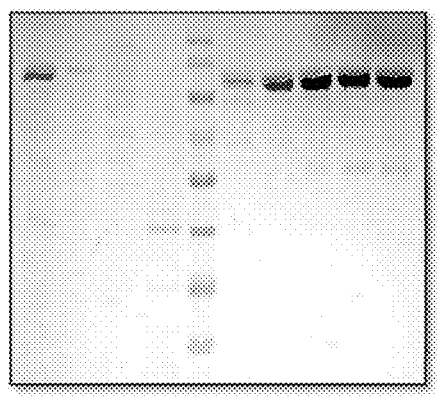
FIG. 9 shows the isolation of CYP450 oxidase BM3.
Figure 10:
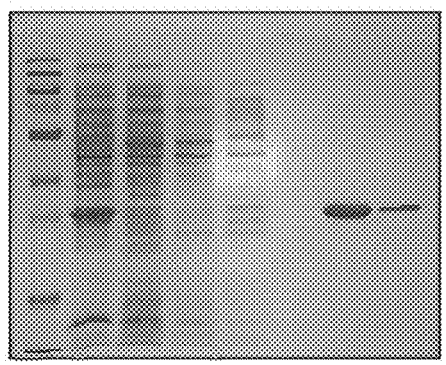
FIG. 10 shows isolation of O-methyltransferase PfOMT.
Figure 11:
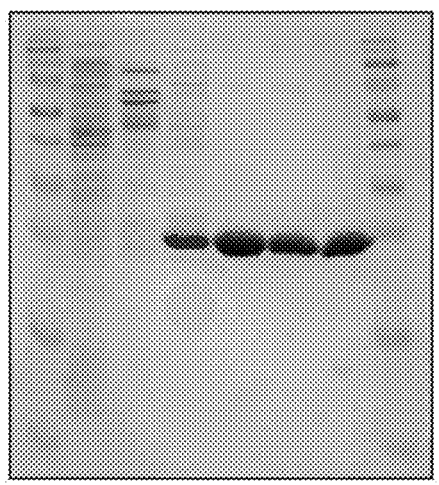
FIG. 11 shows isolation of O-methyltransferase AtCOMT.
Figure 12:
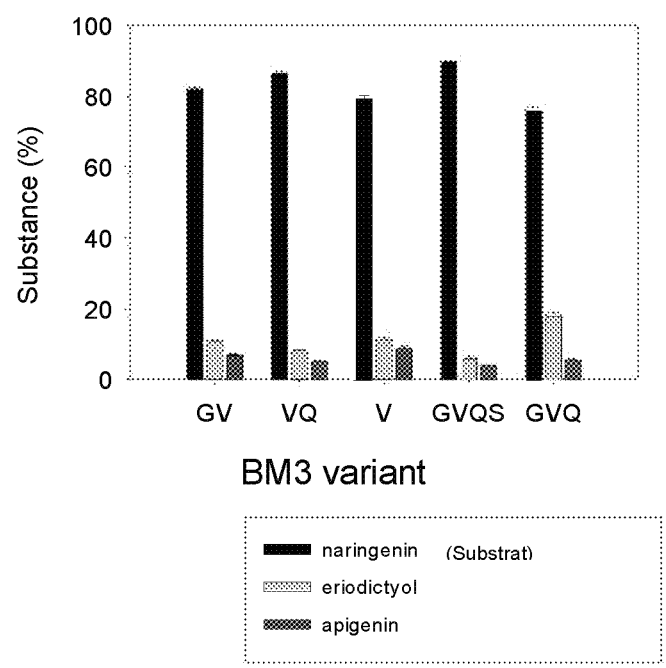
FIG. 12 compares product formation of various variants of BM3.

A first subject-matter of the invention relates to a process for the production of flavonoids, comprising the following steps:

(a) Providing a transgenic microorganism, comprising
   (i) A first nucleic acid fragment (A), comprising or consisting of a gene coding for a CYP450 oxidase,
   (ii) A second nucleic acid fragment (B), comprising or consisting of a gene coding for a plant O-methyltransferase, and
(b) Adding one or more flavanones to the transgenic microorganism,
(c) Converting the flavanones contained in the substrate by the transgenic microorganism to the corresponding flavonoids, and, optionally
(d) Isolating and purifying the final products.

Surprisingly, it was found that by insertion of two different nucleic acid fragments, which contain a gene coding for a bacterial CYP450 oxidase on the one hand and a gene coding for a plant O-methyltransferase on the other into a suitable microorganism, preferably a facultatively anaerobic microorganism, a system is provided which allows the conversion to flavonoids in short times as well as excellent yields after the addition of flavanones and cultivation.

The process is illustrated by means of the example of homoeriodictoyl produced from naringenin in the following scheme:

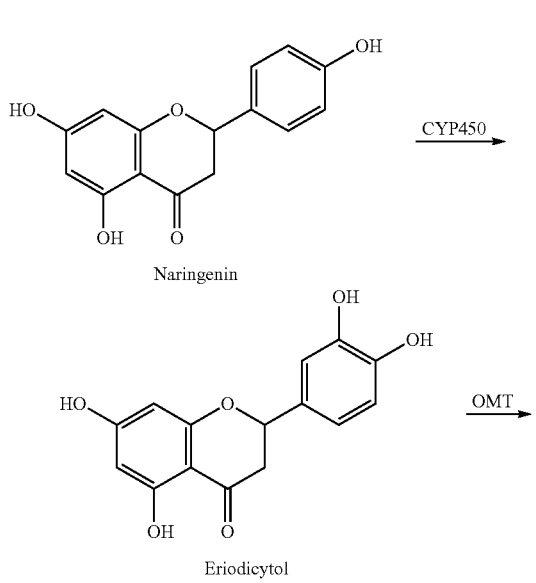

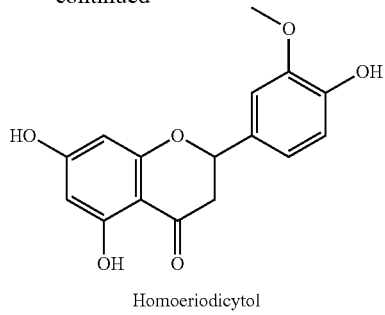

Homoeriodicytol

It was known from the state of the art that naringenin can be converted to eriodictyol by transgenic microorganisms such as, for example, *Sacharomyces cerevisiae*, creating a flavonoid-3'-hydroxylase from *Gerbera hydride* or a CYP450 oxidase from *Phanerochaete chrysosporium* (Kasai, N. et al. "Enzymatic properties of cytochrome P450 catalyzing 3'-hydroxylation of naringenin from the white-rot fungus *Phanerochaete chrysosporium*." Biochem. Biophys. Res. Commun. 387, 103-8 (2009). However, in this case the conversion was carried out up to eriodictyol only, however, a direct further reaction to obtain homoeriodictyol has not been demonstrated yet.

Further processes for the production of eriodictyol from naringenin are published in Kitamura, E. et al. "*Production of Hydroxlated Flavonoids with Cytochrome P450 BM3 Variant F88V and Their Antioxidative Activities*" [Biosci. Biotechnol. Biochem. 77, 1340-1343 (2013)] and Kabumoto, H., Miyazaki, K. & Arisawa, "*A Directed Evolution of the Actinomycete Cytochrome P450 MoxA (CYP105) for Enhanced Activity*" [Biosci. Biotechnol. Biochem. 73, 1922-1927 (2009)]. Furthermore, these are not to be understood as (biotechnological) processes for the production of eriodictyol and/or homoeriodictyol within the meaning of the present invention, particularly not as a process (as described above) suitable for the industrial production of eriodictyol and/or homoeriodictyol, as the yields can be estimated to be very small (e.g., 5.2% in Kitamura et al.).

In addition, the methylation of flavonoids using the enzyme O-methyltransferase from *Bacillus cereus* in which homoeriodictyol is formed from eriodictyol is known from J. Microbiol. Biotech. 16(7), 1090-1096 (2006).

Within the scope of the studies performed in the context of the present invention, it was possible to explain and to characterise critical molecular biological and biochemical principles of biotransformation for the purposes of the process described herein—with the object of producing eriodictyol and/or homoeriodictyol on an industrial scale.

The state of the art describes various enzymatic systems for the formation of eriodictyol based on caffeic acid (Leonard, E., Yan, Y. & Koffas, M. A. G. "*Functional expression of a P450 flavonoid hydroxylase for the biosynthesis of plant-specific hydroxylated flavonols in Escherichia coli*" [Metab. Eng. 8, 172-81 (2006)]. However, these are always based on the biosynthesis path for flavonoids described in plants, wherein naringenin is merely formed as an intermediate product. Further, plant enzymes are used exclusively herein. A synthesis method for the formation of homoeriodicytol or hesperetin based on naringenin is not known yet.

The two international patent applications WO 2006 010117 AI (KOFFAS) and WO 2005 084305 AI (SCHMIDT-DANNERT) describe the application of the heterologous expression for the formation of flavonoids. They (exclusively) describe plant genes which are used for a heterologous expression of various substances (based on L-phenylalanine, tyrosine and cinnamic acid).

Surprisingly, a variant of CYP450 oxidase from *Bacillus megaterium* was identified in the present invention, which could be produced by heterologous expression, and which hydroxylates naringenin regioselectively at the 3' or 5' position. By means of the additional expression of a O-methyltransferase, the conversion of the intermediately formed eriodictyol to homoeriodictyol was advantageously obtained.

CYP450 OXIDASES

A "cytochrome P450 oxidase" (CYP450) within the meaning of the present invention is an enzyme which catalyses the reaction "flavanone⇔3'-hydroxyflavanone". In particular, CYP450 catalyses the reaction of naringenin to obtain eriodictyol (cf. the reaction scheme shown above). Particularly preferred are CYP450 oxidases from the gram-positive bacterium *Bacillus megaterium*.

Therefore, a process is particularly preferred in which the gene coding for a bacterial CYP450 oxidase codes for an oxidase from the microorganism *Bacillus megaterium*.

A particular embodiment of the present invention thus relates to a process characterised in that the nucleic acid fragment (A) introduced into the transgenic microorganism comprises or consists of (i-i) A nucleotide sequence according to SEQ ID NO:1 (nucleotide sequence of the gene coding for the A75G/F88V/L189Q/R472C variant of bacterial CYP450 from *B. megaterium* ATCC 14581) and/or (i-ii) A nucleotide sequence according to SEQ ID NO:2 (nucleotide sequence of the gene coding for the A75G/F88V/L189Q/A331S/R472C variant of bacterial CYP450 from *B. megaterium* ATCC 14581) and/or (i-iii) A similar nucleotide sequence with a nucleotide sequence identity of 40% or more with SEQ ID NO:1 and/or SEQ ID NO:2, preferably of 50% or more, 60 or more, or 80% or more, particularly preferably of 95% or more.

Another subject-matter of the invention, mutatis mutandis, is a process in which the preferably bacterial CYP450 oxidase contains (i-i) A nucleotide sequence according to SEQ ID NO:1 (nucleotide sequence of the gene coding for the A75G/F88V/L189Q/R472C variant of bacterial CYP450 from *B. megaterium* ATCC 14581) and/or (i-ii) A nucleotide sequence SEQ ID NO:2 (nucleotide sequence of the gene coding for the A75G/F88V/L189Q/A331S/R472C variant of bacterial CYP450 from *B. megaterium* ATCC14581) and/or (i-iii) A similar nucleotide sequence with a nucleotide sequence identity of 40% or more with SEQ ID NO:1 and/or SEQ ID NO:2, preferably of 50% or more, 60 or more, or 80% or more, particularly preferably of 95% or more.

Another preferred embodiment of the invention thus relates to a process characterized in that the amino acid fragment (A) introduced into the transgenic microorganism comprises or consists of (i-i) An amino acid sequence according to SEQ ID NO:6 (amino acid sequence of the gene coding for the A75G/F88V/L189Q/R472C variant of bacterial CYP450 from *B. megaterium* ATCC 14581) and/or (i-ii) An amino acid sequence SEQ ID NO:7 (amino acid sequence of the gene coding for the A75G/F88V/L189Q/A331S/R472C variant of bacterial CYP450 from *B. megaterium* ATCC 14581) and/or (i-iii) A similar amino acid sequence with an amino acid sequence identity of 40% or more with SEQ ID NO:6 and/or SEQ ID NO:7, preferably, of 50% or more, 60% or more or 80% or more, particularly preferably of 95% or more.

Another subject-matter of the invention, mutatis mutandis, is a process in which the preferably bacterial CYP450 oxidase contains (i-i) An amino acid sequence according to SEQ ID NO:6 (amino acid sequence of the gene coding for the A75G/F88V/L189Q/R472C variant of bacterial CYP450 from *B. megaterium* ATCC 14581) and/or (i-ii) An amino acid sequence SEQ ID NO:7 (amino acid sequence of the gene coding for the A75G/F88V/L189Q/A331S/R472C variant of bacterial CYP450 from *B. megaterium* ATCC 14581) and/or (i-iii) A similar amino acid sequence with an amino acid sequence identity of 40% or more with SEQ ID NO:6 and/or SEQ ID NO:7, preferably of 50% or more, 60 or more, or 80% or more, particularly preferably of 95% or more.

Within the scope of the present invention, the "nucleic acid and/or amino acid sequence identity" is preferably determined using the Smith Waterman algorithm with a gap open penalty of 10, a gap extension penalty of 0.5 and the BLOSUM62 Matrix (for information on the Smith Waterman algorithm see, for example, Smith, T. F. and Waterman, M. S. "Identification of common molecular subsequences", Journal of Molecular Biology (1981), 147:195-197; implemented online via the corresponding tool page of the EMBL). The submitted nucleotide sequences were created using the software BISSAP of the European Patent Office pursuant to WIPO Standard 25.

O-Methyltransferases

An "O-methyltransferase" (OMT) within the meaning of the present invention is an enzyme which catalyses the regiospecific methylation of particular compounds, in particular the transformation from eriodicytol to hesperetin, sterubin and/or homoeriodictyol (cf. the reaction scheme shown above). Particularly preferred are cation-independent O-methyltransferases from *Mesembryanthemurn crystallinum* or *Arabidopsis thaliana*.

Expressly preferred is therefore a process in which the gene coding for a plant O-methyltransferase codes for an O-methyltransferase from the plant genus *Mesembryanthemum*.

Altogether, particular combinations of CYP450 oxidases and O-methyltransferases are preferred, namely those which are produced from the bacterium *Bacillis megaterium* on the one hand, and from the plants of the species *Mesembryanthemum crystallinum* or *Arabidopsis thaliana* on the other.

A further particular embodiment of the invention therefore relates to a process which is characterised in that the nucleic acid fragment (B) introduced into the transgenic microorganism comprises or consists of (ii-i) A nucleotide sequence according to SEQ ID NO:3 (nucleotide sequence of OMT from *M. crystallinum* (McPFOMT)), and/or (ii-ii) A nucleotide sequence according to SEQ ID NO:4 (nucleotide sequence of O-methyltransferase 1 (OMT1)) and/or (ii-iii) A nucleotide sequence according to SEQ ID NO:5 (nucleotide sequence of O-methyltransferase (AOMT)) and/or (ii-iv) A further nucleotide sequence with a nucleotide sequence identity of 40% or more with SEQ ID NO:3, SEQ ID NO:4 and/or SEQ ID NO:5, preferably of 50% or more, 60% or more, or 80% or more, particularly preferably of 95% or more.

Another subject-matter of the invention, mutatis mutandis, is a process in which the O-methyltransferase contains (ii-i) A nucleotide sequence according to SEQ ID NO:3 (nucleotide sequence of OMT from *M. crystallinum* (McPFOMT)), and/or (ii-ii) A nucleotide sequence according to SEQ ID NO:4 (nucleotide sequence of O-methyltransferase 1 (OMT1)) and/or (ii-iii) A nucleotide sequence according to SEQ ID NO:5 (nucleotide sequence of O-methyltransferase (AOMT)) and/or (ii-vii) A further nucleotide sequence with a nucleotide sequence identity of 40% or more with SEQ ID NO:3, SEQ ID NO:4 and/or SEQ ID NO:5, preferably of 50% or more, 60% or more, or 80% or more, particularly preferably of 95% or more.

A further particular embodiment of the invention therefore relates to a process which is characterised in that an amino acid fragment (B) introduced into the transgenic microorganism comprises or consists of (ii-i) An amino acid sequence according to SEQ ID NO:8 (amino acid sequence of OMT from *M. crystallinum* (McPFOMT)), and/or (ii-ii) An amino acid sequence according to SEQ ID NO:9 (amino acid sequence of O-methyltransferase 1 (OMT1)) and/or (ii-iii) An amino acid sequence according to SEQ ID NO:10 (amino acid sequence of O-methyltransferase (AOMT)) and/or (ii-iv) A further amino acid sequence with an amino acid sequence identity of 40% or more with SEQ ID NO:8, SEQ ID NO:9 and/or SEQ ID NO:10, preferably, of 50% or more, 60% or more, or 80% or more, particularly preferably of 95% or more.

Another subject-matter of the invention, mutatis mutandis, is a process in which the O-methyltransferase contains (ii-i) An amino acid sequence according to SEQ ID NO:8 (amino acid sequence of the OMT from *M. crystallinum* (McPFOMT)), and/or (ii-ii) An amino acid sequence according to SEQ ID NO:9 (amino acid sequence of the O-methyltransferase 1 (OMT1)) and/or (ii-iii) An amino acid sequence according to SEQ ID NO:10 (amino acid sequence of the O-methyltransferase (AOMT)) and/or (ii-vii) A further amino acid sequence with an amino acid sequence identity of 40% or more with SEQ ID NO:8, SEQ ID NO:9 and/or SEQ ID NO:10, preferably of 50% or more, 60% or more or 80% or more, particularly preferably of 95% or more.

Flavanones

The one, several, or all of the flavanones or their preliminary stages or derivatives to be used according to the invention are preferably selected from the group consisting of: naringenin, naringin, narirutin, or other naturally occurring or synthetically produced naringenin glycosides, sakuranetin, sakuranetin glycosides, isosakuranetin, isosakuranetin glycosides, 4',7-dihydroxyflavanone or its glycosides, 4',7-dihydroxy-3'-methoxyflavanone or its glycosides, 3',7-dihydroxy-4'-methoxyflavanone or its glycosides, 3',4',7-trihydroxyflavanone or its glycosides, wherein the flavanones may be present as (S)-, as (R)-enantiomer, as racemate or as any mixture of the two enantiomers with regard to the 2-position of the flavanone structure.

In the following, some of the preferably used flavanones are exemplarily depicted:
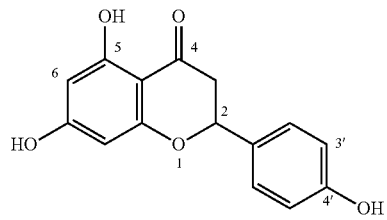
Naringenin
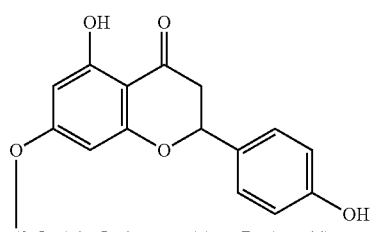
(2-O-alpha-L-rhamnosyl-beta-D-glucosid)
Naringin
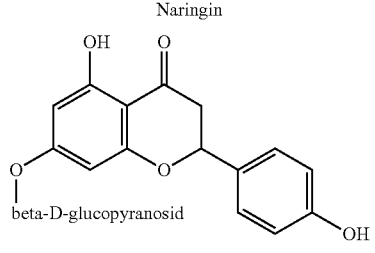
beta-D-glucopyranosid
Narirutin
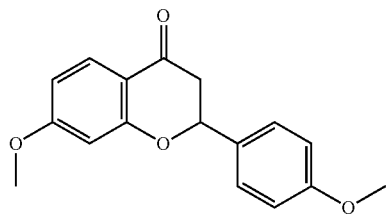
Liquiritigenin
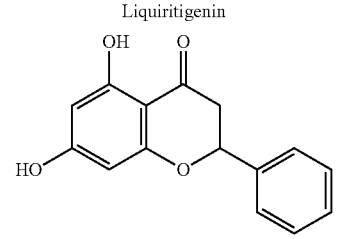
Pinocembrin
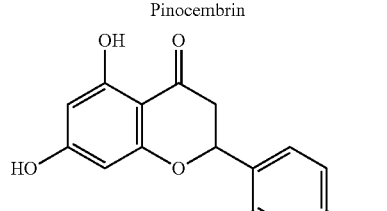
Steppogenin
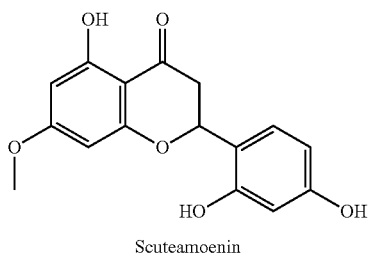
Scuteamoenin
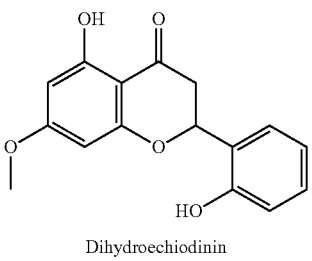
Dihydroechiodinin
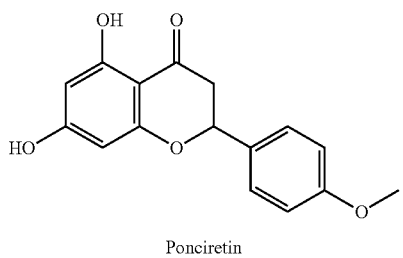
Ponciretin
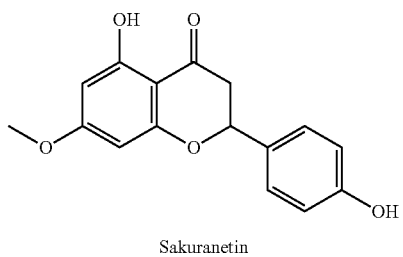
Sakuranetin
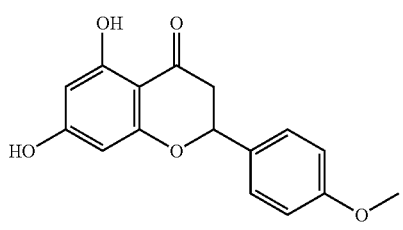
Isosakuranetin
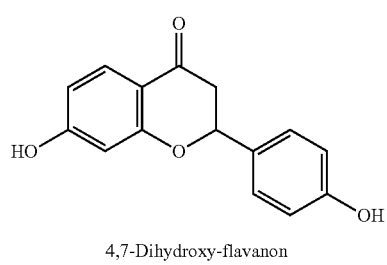
4,7-Dihydroxy-flavanon

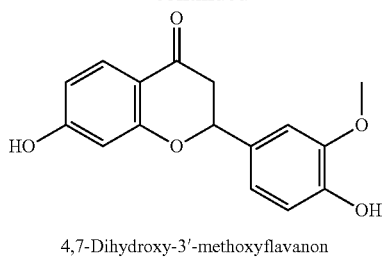

4,7-Dihydroxy-3'-methoxyflavanon

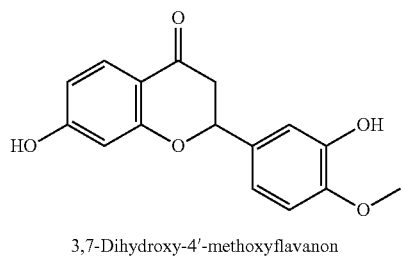

3,7-Dihydroxy-4'-methoxyflavanon

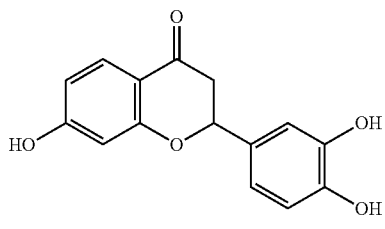

3',4,7-Trihydroxy-flavanon

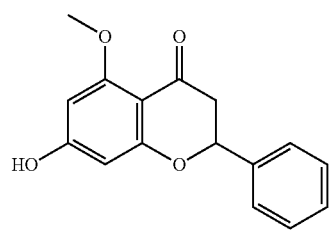

Alpinetin

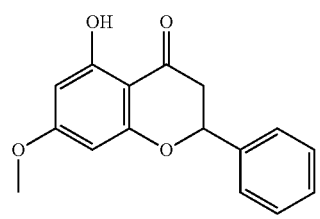

Pinostrobin

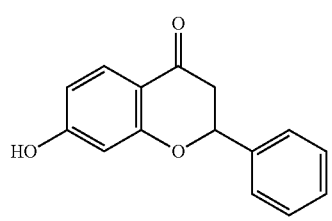

7-Hydroxyflavanon

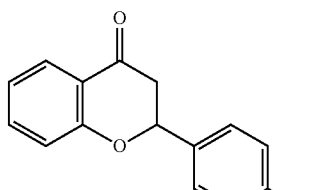

4'-Hydroxyflavanon

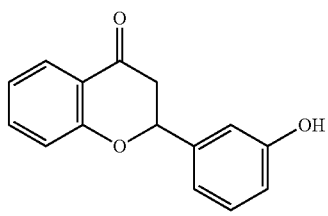

3-Hydroxyflavanon

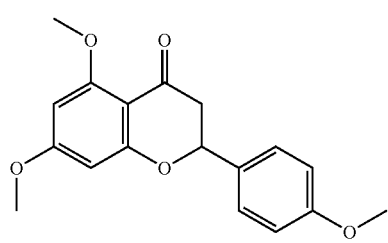

Tsugafolin

The flavonoids to be produced according to the invention are preferably selected from the group consisting of: eriodictyol and the glycosides thereof (e.g., eriocitrin, neoeriocitrin), homoeriodictyol and the glycosides thereof, sterubin and the glycosides thereof, hesperidin, hesperetin and other hesperetin glycosides (e.g., neohesperidin), apigenin and the glycosides thereof, luteolin, diosmetin, chrysoeriol.

In the following, particularly preferred flavonoids according to the invention are depicted:

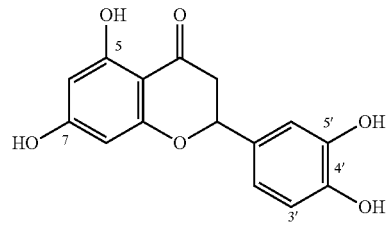

Eriodicytol

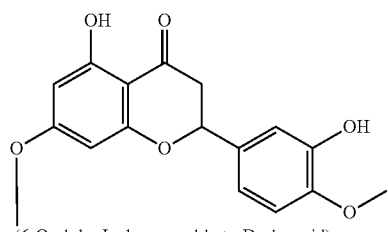

(6-O-alpha-L-rhamnosyl-beta-D-glucosid)
Eriocitrin

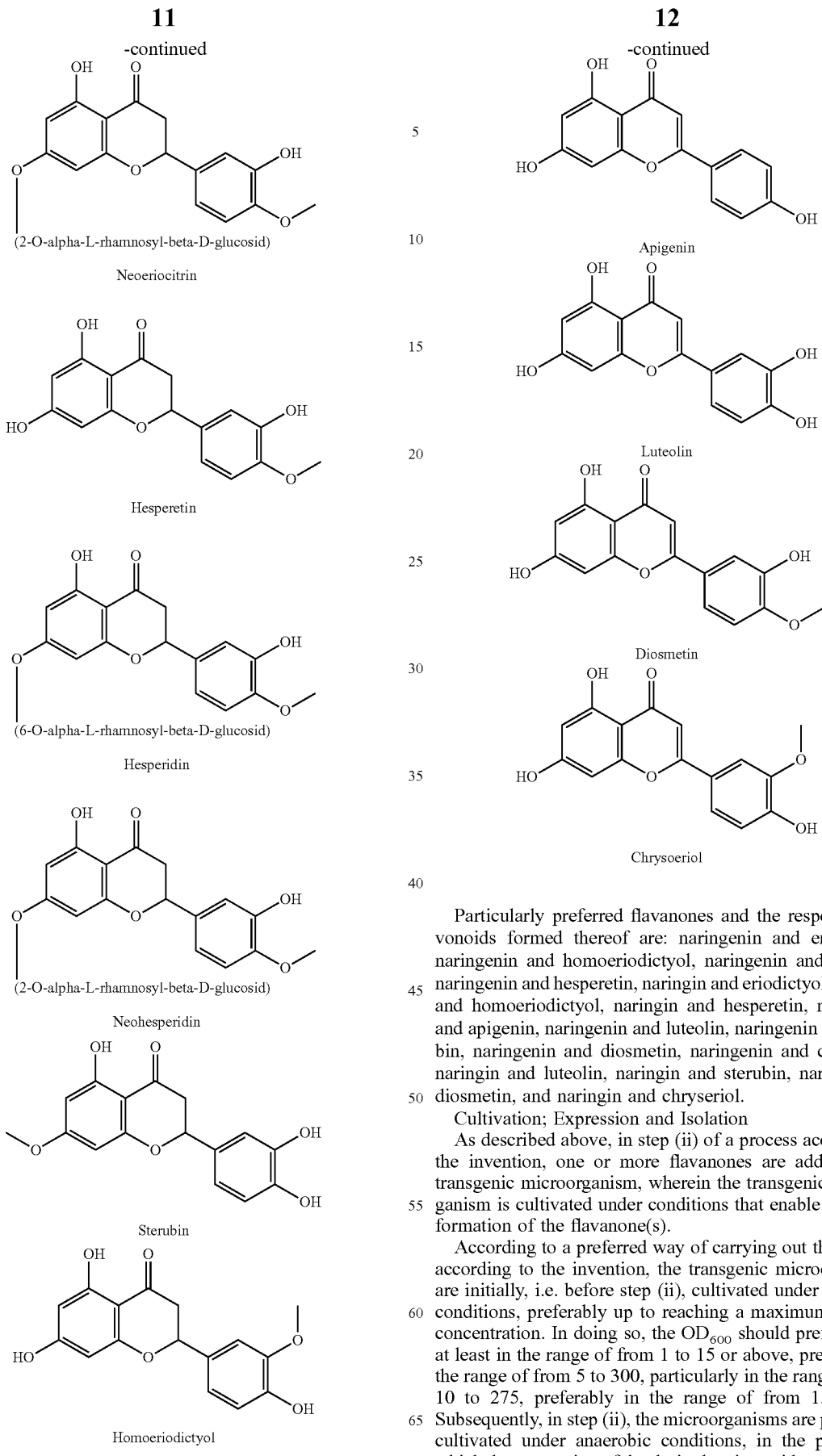

Particularly preferred flavanones and the respective flavonoids formed thereof are: naringenin and eriodictyol, naringenin and homoeriodictyol, naringenin and sterubin, naringenin and hesperetin, naringin and eriodictyol, naringin and homoeriodictyol, naringin and hesperetin, naringenin and apigenin, naringenin and luteolin, naringenin and sterubin, naringenin and diosmetin, naringenin and chryseriol, naringin and luteolin, naringin and sterubin, naringin and diosmetin, and naringin and chryseriol.

Cultivation; Expression and Isolation

As described above, in step (ii) of a process according to the invention, one or more flavanones are added to the transgenic microorganism, wherein the transgenic microorganism is cultivated under conditions that enable the transformation of the flavanone(s).

According to a preferred way of carrying out the process according to the invention, the transgenic microorganisms are initially, i.e. before step (ii), cultivated under anaerobic conditions, preferably up to reaching a maximum biomass concentration. In doing so, the $OD_{600}$ should preferably be at least in the range of from 1 to 15 or above, preferably in the range of from 5 to 300, particularly in the range of from 10 to 275, preferably in the range of from 15 to 250. Subsequently, in step (ii), the microorganisms are preferably cultivated under anaerobic conditions, in the process of which the expression of the desired amino acid sequences or of the desired enzymes is performed on the basis of the introduced nucleic acid fragments or the introduced transgenes, for example, stimulated by means of an induction by IPTG and/or lactose (when using a corresponding suitable promoter or a corresponding, suitable expression system).

In principle, it is preferred according to the invention if the incubation in step (ii) is performed under anaerobic conditions, at least partly or completely.

Depending on the microorganism, the skilled person may, in step (ii), create ambient conditions that are suitable for the purposes of the present invention, providing a suitable (cultivation) medium in particular. Cultivation is, preferably, performed in LB or TB medium. Alternatively, a (more complex) medium, consisting of or comprising plant-based materials, particularly from citrus, grapefruit, and orange plants, may be used. For example, cultivation is performed at a temperature of more than 20° C., preferably of more than 25° C., particularly of more than 30° C. (preferably in the range of from 30 to 40° C.), which may promote the formation of homoeriodictyol from naringenin in particular, or may increase the yield. Further, also a temperature for induction (cf. above) of less than 40° C., particularly of less than 35° C. (particularly in the range of from 20 to 30° C.), may promote the formation of homoeriodictyol or increase the yield.

The flavonoids are added to the transgenic microorganism in step (ii), preferably in an amount of from 0.1 mM to 100 mM (mMol/L), preferably of from 0.5 to 95 mM, particularly preferably of from 1 to 90 mM based on the (cultivation) medium containing the transgenic microorganisms. Here, suitable (co-)solvents may be used.

In case that one or more inductors, e.g., IPTG or lactose are used for induction (e.g., of lac operon), it is preferred to use, in step (ii), the inductor in an amount of from 0.001 to 1 mM, preferably of from 0.005 to 0.9 mM, particularly preferred of from 0.01 to 0.8 mM based on the (cultivation) medium containing the transgenic microorganisms, as particularly good yields may be achieved in this case.

Extractions may be performed, for example, with organic solvents in order to isolate or purify the expressed flavonoids. These are preferably selected from the following list: isobutane, 2-propanol, toluol, methyl acetate, cyclohexane, 2-butanol, hexane, 1-propanol, light petroleum, 1,1,1,2-tetrafluoroethane, methanol, propane, 1-butanol, butane, ethyl methyl ketone, ethyl acetate, diethyl ether, ethanol, dibutyl ether, CO2, tert. butyl methyl ether, acetone, dichloromethane and N2O. Particularly preferred are those solvents which form a visually perceivable phase boundary with water. Accordingly, a removal of the residual water within the solvent and the removal of the solvent itself may suggest itself, which may be followed by re-dissolving the dihydrochalcone in an (optionally other) solvent which may be suitable, for example, for any optional subsequent crystallisation and drying of the product. Alternatively or additionally, an adsorptive, distillative and/or chromatographic purification may be performed.

Alternatively, methods for drying, particularly methods of vacuum belt drying, spray drying, destillation or lyphilisation of the cell-containing or cell-free fermentation solution may be used in order to isolate or purify the formed flavonoids.

Transgenic Microorganisms

In the context of the present invention, a "transgenic microorganism" is to be understood as a genetically changed or modified microorganism, into which nucleic acid fragments (see nucleic acid fragments (A) and (B) as described herein) or genes of another organism (so-called transgenes) have been selectively introduced by means of biotechnological processes.

A further subject-matter of the invention thus comprises a transgenic microorganism, containing
  (i) A first nucleic acid fragment (A), containing a gene coding for a bacterial CYP450 oxidase, and
  (ii) A second nucleic acid fragment (B), containing a gene coding for a plant O-methyltransferase.

This is preferably a microorganism selected from the group consisting of facultatively anaerobic microorganisms, particularly, of facultatively anaerobic bacteria, preferably proteobacteria, particlarly, enterobacteria, for example, of the genus *Escherichia*, preferably, *E. coli*, particularly, *E. coli* K12, *E. coli* BL21 and *E. coli* MG1655 and their derivatives, yeasts, for example, *S. cerevesiae* and *P. pastoris, K. lactis, H. polymorpha*, and fungi such as *Aspergillus* spp. or *Trichoderma* spp.

The transgenic microorganism according to the invention is particularly characterised in that
  (i) The gene coding for a CYP450 oxidase codes for a CYP450 oxidase from the microorganism *Bacillus megaterium* (BM3), preferably for the F88V variant of BM3, particularly for the A75G/F88V variant of BM3, particularly preferably for the variant A75G/F88V/L189Q/R472C of BM3, or for the variant A75G/F88V/L189Q/A331S/R472C of BM3, and/or
  (ii) The gene coding for an O-methyltransferase codes for an O-methyltransferase from a plant of the order Brassicales, preferably from the Brassicaceae family, preferably from the Camelineae sub-family, particularly, the genus of *Arabidopsis*, especially the species *Arabidopsis thaliana*, or from the order Caryophyllales, preferably, the family Aizoaceae, preferably, the sub-family Mesembryanthemoideae, particularly, the genus *Mesembryanthemum*, especially from the species *Mesembryanthemum crystallinum*, i.e., particularly preferred for an O-methyltransferase from *M. thaliana* or *M. crystallinum*.

Methods to enable an expression of the desired amino acid sequences or of the desired enzymes on the basis of the introduced nucleic acid fragments or transgenes are sufficiently known to the skilled person, e.g., using a regulatory element, particularly a promotor.

Vector

A further aspect of the present invention relates to a vector, i.e. a transport vehicle ("gene shuttle") for the transfer of (a) foreign nucleic acid(s) into a recipient cell, particularly a plasmid vector, enabling the cloning of one or more nucleic acid fragments, containing
  (i) A first nucleic acid fragment (A), containing a gene coding for a bacterial CYP450 oxidase, and
  (ii) A second nucleic acid fragment (B), containing a gene coding for a plant O-methyltransferase.

The invention also comprises a vector, preferably a plasmid vector, characterised in that it has
  (i) A first nucleic acid fragment (A), containing a gene coding for a bacterial CYP450 oxidase, and
  (ii) A second nucleic acid fragment (B), containing a gene coding for a plant O-methyltransferase.

Besides the nucleic acid fragment(s) (A) and (B), a vector according to the invention may optionally contain further common components for the purposes of the present invention, particularly those improving or, where necessary, enabling the expression of the transgenes described herein in microorganisms, particularly in those as described above. In principle, a vector according to the invention preferably also contains one or more further components or elements selected from the group consisting of promotor, on-sequence, sequence for affinity chromatographic purification, selectable markers, operator sequence, terminator, ribosomal binding sites, protease cleavage sequence, recombination binding sites, sequences of fusion proteins and chaperone sequences.

Host Cell

The present invention also relates to a host cell, containing one or more identical or different vectors according to the invention as described herein.

A host cell according to the invention is preferably a microorganism (as described above) according to the invention or a microorganism to be used according to the invention. The host cells according to the invention described herein, or the microorganisms according to the invention, or microorganisms to be used according to the invention preferably are or serve as a (production) strain for the biotechnological production of the flavonoids described herein, particularly of eriodictyol, hesperetin, sterubin and/or homoeriodictyol.

Preparations

By means of the process according to the invention, flavanones may thus be converted to flavonoids using biotechnological methods, and are characterised in that they taste less bitter and more sweet than the original preparation, and are permitted to be designated as natural or nature-identical at the same time.

Therefore, a further subject-matter of the invention is directed to food preparations, containing flavonoids obtained according to the process according to the invention or a process for improving the taste of the flavanone-containing food, comprising the conversion of the food by the process described above.

The flavanone-containing foods or preparations suitable for food production such obtained are then converted by the process according to the invention to flavanoid-containing preparations which may be designated as natural and may then be used as such or, after removal of the host cell and/or its components and optional concentration by means of physical processes, as a preparation suitable for food production, preferably as a preparation suitable for food production with a bitter-masking or sweet-enhancing effect.

Examples for suitable foods particularly comprise confectionary (for example, chocolates, chocolate bar products, other bar products, fruit gum, hard and soft caramels, chewing gum) alcoholic or nonalcoholic beverages (e.g. coffee, tea, wine, wine-containing beverages, beer, beer-containing beverages, liqueurs, schnapps, brandies, (carbonated) fruit-containing lemonades, (carbonated) isotonic beverages, (carbonated) soft drinks, nectars, spritzers, fruit and vegetable juices, fruit or vegetable juice preparations and instant beverages (for example, instant cocoa beverages, instant tea beverages, instant coffee beverages, instant fruit beverages).

Herein, citrus juices, particularly orange juices which contain a high content in naringin and which may be converted by the process according to the invention to flavonoid-containing orange juices according to the invention are particularly preferred as flavanone-containing foods.

EXAMPLES

Example 1

Providing Transgenic Microorganisms (cf. Step (i))
Transformation

50 µl aliquoted chemically competent E. coli BL21(DE) cells were incubated on ice for 5 minutes. After adding 100 ng plasmid DNA (pSYM_BM3), the suspension was stirred and incubated on ice for a further 10 minutes. The transformation was performed by transferring the suspension to a water bath at 42° C. for 30 s, and subsequently to ice water for 5 min. Then, 250 µl S.O.C. medium was added, and the cells were cultivated at 37° C. and 200 rpm for 1 h. Finally, 200 µl of the culture was spread on LB agar containing the corresponding antibiotic. The petri dish was incubated at 37° C. for 14 h.

Mutagenesis

The QuikChange II Site-Directed Mutagenesis Kit by the company Agilent was used. By means of specific primers (Table 1), which contain the desired mutation including flanking unmodified regions, a PCR was performed using the BM3 plasmid DNA. Subsequently, the PCR reaction mixture was placed on ice for 2 minutes. Then, 10 U Dpn I was added, in the process of which the reaction is incubated at 37° C. for 1 h. The primer sequences for the mutagenesis are shown in Table 1.

TABLE 1

| Primer sequences for mutagenesis | |
|---|---|
| BM3_75G_fwd | TTGATAAAAACTTAAGTCAAGGTCTTAAAT TTGTACGTGATTT |
| BM3_75G_rev | AAA\|CACG\|ACAAA\|1\|AAGACC\|\|GAC\|\| AAG\|111\|A\|CAA |
| BM3_189Q_fwd | TGGATGAAGCAATGAACAAGCAGCAGCGAG CAAATCCAGACGA |
| BM3_189Q_rev | TCGTCTGGATTTGCTCGCTGCTGCTTGTTC ATTGCTTCATCCA |
| BM3_331S_fwd | TATGGCCAACTGCTCCTTCGTTTTCCCTAT |
| BM3_331S_rev | ATAGGGAAAACGAAGGAGCAGTTGGCCATA |

Example 2

Biotechnological Production of Eriodictyol (cf. Step (ii))
Enzymatic Production of Eriodicytol 200 µM naringenin were dissolved in 50 mM tris-buffered saline, pH 7.5, and incubated together with 5 mM glucose 6-phosphate, 14 U glucose 6-phosphate dehydrogenase, 100 µM NADPH and 50 µL cell extract (0.5-1 µM CYP450) in a total volume of 1 mL for 14 h at 25° C. and 200 rpm. Subsequently, the reaction solution was extracted twice with 500 µL ethyl acetate, in the process of which the organic phases were combined and the solvent was removed in vacuum.

Fermentative Production of Eriodicytol

E. coli BL21 (DE3) cells transformed with pSYM_BM3 were cultivated in LB medium up to an optical density at 600 nm of 0.7, and the protein production was induced by adding 1 mM Isopropyl-ß-D-thiogalactopyranoside. After an incubation time of 3 h, the cultures were directly reacted with 200 µM eriodictyol and incubated for 14 h at 37° C. The cultures were centrifuged at 20,000×g for 10 min and extracted with the triple volume of ethyl acetate, the organic phase was washed with a saturated sodium chloride solution, and the solvent was destilled in vacuum.

Example 3

Biotechnological Production of Homoeriodictyol and/or Hesperetin (cf. Step (ii))
Enzymatic Production of Homoeriodicytol 20 µM eriodicytol were dissolved in 50 mM potassium phosphate buffer, pH 7.5 and incubated together with 1 µM PfOMT, 250 μM magnesium chloride and 1 mM S-adenosylmethionine at 37° C. and 200 rpm for 10 minutes. Subsequently, the reaction solvent was extracted twice with 500 μL ethyl acetate, in the process of which the organic phases were combined and the solvent was removed in vacuum.

Fermentative Production of Homoeriodicytol (cf. Step (ii))

Cells transformed with pSYM_BM3 and pSYM_PfOMT were inoculated in ZYM-5052 1:20 with starter culture and 200 μM naringenin, and incubated at 38° C. and 200 rpm for 24 h. The course of the optical density, of the gene expression and of the substrate turnover was monitored by regular taking of 1 mL samples. For analysis, the cells were harvested by means of centrifugation at 14.000×g for 10 minutes, and lysis was performed by means of 150 μL B-PER II reagent (Thermo Scientific, Rockford) with 50 μL DNAse I according to manufacturer's indications. The samples obtained were analysed by means of SDS polyacrylamide gel electrophoresis. For analysis of the substrate conversion, 1 mL of the culture were extracted twice with 500 μL ethyl acetate, in the process of which the organic phases were combined and the solvent was removed in vacuum. Subsequently, the samples were incorporated into acetonitrile and analysed by means of HPLC and UPLC-MS/MS.

Enzymatic Production of Hesperetin

20 μM eriodicytol were dissolved in 50 mM potassium phosphate buffer, pH 7.5 and incubated together with 1 μM AOMT, 250 μM Magnesiumchlorid and 1 mM S-adenosylmethionine at 37° C. and 200 rpm for 10 minutes. Subsequently, the reaction solution was extracted twice with 500 μL ethyl acetate, in the process of which the organic phases were combined and the solvent was removed in vacuum.

Fermentative Production of Hesperetin

Cells transformed with pSYM_BM3 and pSYM_AOMT were inoculated in ZYM-5052 1:20 with starter culture as well as with 200 μM naringenin and incubated at 38° C. and 200 rpm for 24 h. The course of the optical density, of the gene expression and of the substrate turnover was monitored by regular taking of 1 mL samples. For analysis, the cells were harvested by means of centrifugation at 14,000×g for 10 minutes, and lysis was performed by means of 150 μL B-PER II reagent (Thermo Scientific, Rockford) with 50 μL DNAse I according to manufacturer's indications. The samples obtained were analysed by means of SDS polyacrylamide gel electrophoresis. For analysis of the substrate conversion, 1 mL of the culture was extracted twice with 500 μL ethyl acetate, in the process of which the organic phases were combined and the solvent was removed in vacuum. Subsequently, the samples were incorporated into acetonitril and analysed by means of HPLC and UPLC-MS/MS.

The invention claimed is:

1. A process for the production of flavonoids, comprising:
   (a) adding one or more flavanones selected from naringenin and naringin to a transgenic microorganism, the transgenic microorganism comprising a first nucleic acid segment (A), comprising the nucleotide sequence set forth as SEQ ID NO:1 and/or the nucleotide sequence set forth as SEQ ID NO:2 and/or a nucleotide sequence at least 95% identical to SEQ ID NO:1 and/or SEQ ID NO:2 and which codes for a CYP450 oxidase that catalyzes the conversion of naringenin to eriodictyol and which comprises A75G, F88V, L189Q, and R472C amino acid substitutions and/or comprises A75G, F88V, L189Q, A331S and R472C amino acid substitutions, the numbering of amino acid residues being in accordance with that of SEQ ID NO:6, and a second nucleic acid segment (B), comprising a gene having the nucleotide sequence set forth as SEQ ID NO:3 or having a nucleotide sequence at least 95% identical to the nucleotide sequence set forth as SEQ ID NO:3 and which codes for a plant O-methyltransferase that catalyzes the conversion of eriodictyol to hesperetin, whereby the flavanones naringenin and/or naringin are converted to the corresponding flavonoid(s) eriodictyol, homoeriodictyol, hesperetin, sterubin, apigenin, luteolin, diosmetin, and/or chryseriol by the transgenic microorganism, and optionally
   (b) isolating and purifying the end products.

2. An enzymatic process for the production of flavonoids, comprising the following steps:
   (a) providing
      (i) a first CP450 oxidase enzyme that catalyzes the conversion of naringenin to eriodictyol and which comprises A75G, F88V, L189Q, and R472C amino acid substitutions and/or comprises A75G, F88V, L189Q, A331S and R472C amino acid substitutions, the numbering of amino acid residues being in accordance with that of SEQ ID NO:6, and
      (ii) a second plant O-methyltransferase enzyme encoded by a gene having the nucleotide sequence set forth as SEQ ID NO:3 or a sequence at least 95% identical to the nucleotide sequence set forth as SEQ ID NO:3 and which catalyzes the conversion of eriodictyol to hesperetin,
   (b) adding one or more flavanones selected from naringenin and naringin to the reaction of (a),
   (c) converting the flavanones naringenin and/or naringin to the corresponding flavonoid(s) eriodictyol, homoeriodictyol, hesperetin, sterubin, apigenin, luteolin, diosmetin, and/or chryseriol by first and/or the second enzyme, and optionally
   (d) isolating and purifying the end products.

3. The process of claim 1, wherein the transgenic microorganism comprises a first nucleic acid segment (A), comprising the nucleotide sequence set forth as SEQ ID NO:1 and/or the nucleotide sequence set forth as SEQ ID NO:2 and a second nucleic acid segment (B), comprising a gene coding for a plant O-methyltransferase having the nucleotide sequence set forth as SEQ ID NO:3.

4. The process of claim 1, wherein the gene coding for a bacterial CYP450 oxidase codes for an oxidase from the microorganism *Bacillus megaterium*.

5. The process of claim 1, wherein the gene coding for a plant O-methyltransferase codes for an O-methyltransferase from the plant genus *Mesembryanthemum*.

6. The process of claim 1, wherein the microorganism is a facultatively anaerobic microorganism.

* * * * *

SEQUENCE LISTING

```
<160> NUMBER OF SEQ ID NOS: 16

<210> SEQ ID NO 1
<211> LENGTH: 3150
<212> TYPE: DNA
<213> ORGANISM: Bacillus megaterium ATCC 145811
<220> FEATURE:
<223> OTHER INFORMATION: BM3 GVQ

<400> SEQUENCE: 1
atgacaatta aagaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg tcgtgtaacg cgctacttat caagtcagcg tctaattaaa     180
gaagcatgcg atgaatcacg ctttgataaa aacttaagtc aaggtcttaa atttgtacgt     240
gattttgcag gagacgggtt ggttacaagc tggacgcatg aaaaaaattg gaaaaaagcg     300
cataatatct tacttccaag cttcagtcag caggcaatga aaggctatca tgcgatgatg     360
gtcgatatcg ccgtgcagct tgttcaaaag tgggagcgtc taaatgcaga tgagcatatt     420
gaagtaccgg aagacatgac acgtttaacg cttgataaca ttggtctttg cggctttaac     480
tatcgcttta acagcttta ccgagatcag cctcatccat ttattacaag tatggtccgt     540
gcactggatg aagcaatgaa caagcagcag cgagcaaatc cagacgaccc agcttatgat     600
gaaaacaagc gccagtttca agaagatatc aaggtgatga cgacctagt agataaaatt     660 attgcagatc gcaaagcaag cggtgaacaa agcgatgatt tattaacgca tatgctaaac     720
ggaaaagatc cagaaacggg tgagccgctt gatgacgaga acattcgcta tcaaattatt     780
acattcttaa ttgcgggaca cgaaacaaca agtggtcttt tatcatttgc gctgtatttc     840
ttagtgaaaa atccacatgt attacaaaaa gcagcagaag aagcagcacg agttctagta     900
gatcctgttc aagctacaa acaagtcaaa cagcttaaat atgtcggcat ggtcttaaac     960
gaagcgctgc gcttatggcc aactgctcct gcgtttttcc tatatgcaaa agaagatacg    1020
```

```
gtgcttggag gagaatatcc tttagaaaaa ggcgacgaac taatggttct gattcctcag    1080
cttcaccgtg ataaaacaat tggggagac gatgtggaag agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctggata ttaagaaac tttaacgtta    1320 aaacctgaag ctttgtggt aaaagcaaaa tcgaaaaaa ttccgcttgg cggtattcct    1380
tcacctagca ctgaacagtc tgctaaaaaa gtatgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taagtagag    2340 cttgaagcct tgcttgaaaa gcaagccta aaagaacaag tgctggcaaa cgtttaaca    2400 atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa agacgtgtg ggctgggtaa                                     3150
```

<210> SEQ ID NO 2
<211> LENGTH: 3150
<212> TYPE: DNA
<213> ORGANISM: Bacillus megaterium ATCC 145811
<220> FEATURE:
<223> OTHER INFORMATION: BM3 GVQS

<400> SEQUENCE: 2

```
atgacaatta aagaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg tcgtgtaacg cgctacttat caagtcagcg tctaattaaa     180
gaagcatgcg atgaatcacg cttttgataaa aacttaagtc aaggtcttaa atttgtacgt     240
gattttgcag gagacgggtt ggttacaagc tggacgcatg aaaaaaattg gaaaaaagcg     300
cataatatct tacttccaag cttcagtcag caggcaatga aaggctatca tgcgatgatg     360
gtcgatatcg ccgtgcagct tgttcaaaag tgggagcgtc taaatgcaga tgagcatatt     420
gaagtaccgg aagacatgac acgtttaacg cttgatacaa ttggtctttg cggctttaac     480
tatcgcttta acagctttta ccgagatcag cctcatccat ttattacaag tatggtccgt     540
gcactggatg aagcaatgaa caagcagcag cgagcaaatc cagacgaccc agcttatgat     600
gaaaacaagc gccagtttca agaagatatc aaggtgatga cgacctagt agataaaatt     660
attgcagatc gcaaagcaag cggtgaacaa agcgatgatt tattaacgca tatgctaaac     720
ggaaaagatc cagaaacggg tgagccgctt gatgacgaga acattcgcta tcaaattatt     780
acattcttaa ttgcgggaca cgaaacaaca agtggtctt tatcatttgc gctgtatttc     840
ttagtgaaaa atccacatgt attacaaaaa gcagcagaag aagcagcacg agttctagta     900
gatcctgttc aagctacaa acaagtcaaa cagcttaaat atgtcggcat ggtcttaaac     960
gaagcgctgc gcttatggcc aactgctcct tcgttttccc tatatgcaaa agaagatacg    1020
gtgcttggag gagaatatcc tttagaaaaa ggcgacgaac taatggttct gattcctcag    1080
cttcaccgtg ataaaacaat ttggggagac gatgtggaag agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact tgaagatca tacaaactac gagctggata ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtatgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg cgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aagaacttc aacagccagg cagtgcacga    2040
agcacgcgac atcttgaaat tgaacttcca aagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taagtagag    2340
```

| | |
|---|---|
| cttgaagcct tgcttgaaaa gcaagcctac aaagaacaag tgctggcaaa acgtttaaca | 2400 |
| atgcttgaac tgcttgaaaa atacccggcg tgtgaaatga aattcagcga atttatcgcc | 2460 |
| cttctgccaa gcatacgccc gcgctattac tcgatttctt catcacctcg tgtcgatgaa | 2520 |
| aaacaagcaa gcatcacggt cagcgttgtc tcaggagaag cgtggagcgg atatggagaa | 2580 |
| tataaggaa ttgcgtcgaa ctatcttgcc gagctgcaag aaggagatac gattacgtgc | 2640 |
| tttatttcca caccgcagtc agaatttacg ctgccaaaag accctgaaac gccgcttatc | 2700 |
| atggtcggac cgggaacagg cgtcgcgccg tttagaggct tgtgcaggc gcgcaaacag | 2760 |
| ctaaaagaac aaggacagtc acttggagaa gcacatttat acttcggctg ccgttcacct | 2820 |
| catgaagact atctgtatca agaagagctt gaaaacgccc aaagcgaagg catcattacg | 2880 |
| cttcataccg cttttctcg catgccaaat cagccgaaaa catacgttca gcacgtaatg | 2940 |
| gaacaagacg gcaagaaatt gattgaactt cttgatcaag gagcgcactt ctatatttgc | 3000 |
| ggagacggaa gccaaatggc acctgccgtt gaagcaacgc ttatgaaaag ctatgctgac | 3060 |
| gttcaccaag tgagtgaagc agacgctcgc ttatggctgc agcagctaga agaaaaaggc | 3120 |
| cgatacgcaa aagacgtgtg ggctgggtaa | 3150 |

<210> SEQ ID NO 3
<211> LENGTH: 714
<212> TYPE: DNA
<213> ORGANISM: Mesembryanthemum crystallinum
<220> FEATURE:
<223> OTHER INFORMATION: McPFOMT

<400> SEQUENCE: 3

| | |
|---|---|
| atggattttg ctgtgatgaa gcaggtcaaa aatacaggat tgctacagag tgaggagtta | 60 |
| tgccagtata ttctccgaac tagtgtctat ccgcgagaag cagggttcct caaggaactc | 120 |
| agggaagcca atgaaagtca cccagactct tatatgtcga cttcaccact tgctggacaa | 180 |
| ttgatgtcat tcgttctaaa attagtgaat gcaaagaaga ctattgaagt tggagtcttt | 240 |
| acaggatact ccctcttact cactgctctt tcaattcctg atgatggaaa gattacggca | 300 |
| attgatttcg acagagaggc atatgagatt ggcttgccat ttatcagaaa agctggtgtg | 360 |
| gagcacaaaa tcaacttcat tgaatcggat gctatgctag ctcttgacaa tcttctgcaa | 420 |
| ggacaagaga gcgaggggag ttacgacttt ggctttgttg atgcggacaa acctaactac | 480 |
| atcaagtacc atgagaggtt gatgaaacta gtcaaggtgg gtggcatagt cgcttatgac | 540 |
| aacacattat ggggtggaac tgtagcccag cctgaatccg aagtaccaga tttcatgaag | 600 |
| gaaaacagag aagctgttat tgaactcaac aagttgcttg ctgctgatcc tcgtatcgag | 660 |
| attgtacatc ttcctttggg tgatggtatc actttctgca ggcgtcttta ttga | 714 |

<210> SEQ ID NO 4
<211> LENGTH: 1092
<212> TYPE: DNA
<213> ORGANISM: Mesembryanthemum crystallinum
<220> FEATURE:
<223> OTHER INFORMATION: AtCOMT

<400> SEQUENCE: 4

| | |
|---|---|
| atgggttcaa cggcagagac acaattaact ccggtgcaag tcaccgacga cgaagctgcc | 60 |
| ctcttcgcca tgcaactagc cagtgcttcc gttcttccga tggctttaaa atccgcctta | 120 |
| gagcttgacc tcttgagat tatggccaag aatggttctc ccatgtctcc taccgagatc | 180 |
| gcttctaaac ttccgaccaa aaatcctgaa gctccggtca tgctcgaccg tatcctccgt | 240 |

```
cttcttacgt cttactccgt cttaacctgc tccaaccgta aactttccgg tgatggcgtt    300
gaacggattt acgggcttgg tccggtttgc aagtatttga ccaagaacga agatggtgtt    360
tccattgctg ctctttgtct tatgaaccaa gacaaggttc tcatggaaag ctggtaccat    420
ttgaaggatg caattcttga tggtgggatt ccattcaaca aggcttatgg aatgagcgcg    480
ttcgagtacc acgggactga ccctagattc aacaaggtct ttaacaatgg aatgtctaac    540
cattccacaa tcaccatgaa gaagattctt gagacctata agggttttga aggattgact    600
tctttggttg atgttggtgg tggcattggt gctacactca aaatgattgt ctccaagtac    660
cctaatctta aaggcatcaa ctttgatctc ccacatgtca tcgaagatgc tccttctcat    720
cctggtattg agcatgttgg aggagatatg tttgtaagtg tccctaaagg tgatgccata    780
ttcatgaagt ggatatgtca tgactggagt gacgaacatt gcgtgaaatt cttgaagaac    840
tgctacgagt cacttccaga ggatggaaaa gtgatattag cagagtgtat acttccagag    900
acaccagact caagcctctc aaccaaacaa gtagtccatg tcgattgcat tatgttggct    960
cacaatcccg gaggcaaaga acgaaccgag aaagagtttg aggcattagc caaagcatca   1020
ggcttcaagg gcatcaaagt tgtctgcgac gcttttggtg ttaaccttat tgagttactc   1080
aagaagctct aa                                                       1092

<210> SEQ ID NO 5
<211> LENGTH: 699
<212> TYPE: DNA
<213> ORGANISM: Mesembryanthemum crystallinum
<220> FEATURE:
<223> OTHER INFORMATION: AOMT

<400> SEQUENCE: 5
atggctaagg atgaagccaa gggattgctg aaaagtgaag agctctataa atatatactg     60
gagactagtg tgtacccacg cgagccagag gttctcaggg agcttaggaa cattactcat    120
aaccaccctc aagctggtat ggctactgca ccagacgctg gccagttgat ggggatgctg    180
ctgaatctgg taaatgcaag aaagactatc gaggttgggg ttttcactgg atactctctt    240
ctcctcactg ctcttacgct accagaagat ggcaaggtta tcgccattga catgaataga    300
gactcgtatg aaataggatt gccggttata agaaagctg gtgttgaaca caaaattgat    360
ttcaaagagt ctgaagctct tccagccctc gacgagcttt taaacaataa agtgaatgag    420
ggtggattcg acttcgcatt tgtggatgca gacaagctga attattggaa ctatcatgag    480
aggcttatta gattgatcaa agttggtggg atcatagtgt atgataacac tctctgggga    540
ggatcagttg ctgaaccgga ctcgtccacg cccgagtgga ggatagaagt caagaaagca    600 acctcgagc tgaacaagaa actctcggct gatcagcgtg tgcagatctc gcaagctgcg    660
cttggcgatg gtatcactat ttgcaggagg ttatattga                          699

<210> SEQ ID NO 6
<211> LENGTH: 1049
<212> TYPE: PRT
<213> ORGANISM: Bacillus megaterium ATCC 145811
<220> FEATURE:
<223> OTHER INFORMATION: BM3 GVQ

<400> SEQUENCE: 6

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30
```

-continued

```
Ile Ala Asp Glu Leu Gly Glu Ile Phe Lys Phe Glu Ala Pro Gly Arg
         35                  40                  45

Val Thr Arg Tyr Leu Ser Ser Gln Arg Leu Ile Lys Glu Ala Cys Asp
 50                  55                  60

Glu Ser Arg Phe Asp Lys Asn Leu Ser Gln Gly Leu Lys Phe Val Arg
 65                  70                  75                  80

Asp Phe Ala Gly Asp Gly Leu Val Thr Ser Thr His Glu Lys Asn
             85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Val
                115                 120                 125

Gln Lys Trp Glu Arg Leu Asn Ala Asp Glu His Ile Glu Val Pro Glu
         130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Gln Gln Arg Ala
                180                 185                 190

Asn Pro Asp Asp Pro Ala Tyr Asp Glu Asn Lys Arg Gln Phe Gln Glu
         195                 200                 205

Asp Ile Lys Val Met Asn Asp Leu Val Asp Lys Ile Ile Ala Asp Arg
210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
         275                 280                 285

Gln Lys Ala Ala Glu Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Leu Met Val Leu Ile Pro Gln Leu His Arg Asp Lys Thr Ile Trp
         355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
         435                 440                 445
```

```
Ala Lys Ser Lys Lys Ile Pro Leu Gly Gly Ile Pro Ser Pro Ser Thr
    450                 455                 460
Glu Gln Ser Ala Lys Lys Val Cys Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
                515                 520                 525
Ala Val Leu Ile Val Thr Ala Ser Tyr Asn Gly His Pro Pro Asp Asn
530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
                580                 585                 590
Lys Gly Ala Glu Asn Ile Ala Asp Arg Gly Glu Ala Asp Ala Ser Asp
            595                 600                 605
Asp Phe Glu Gly Thr Tyr Glu Glu Trp Arg Glu His Met Trp Ser Asp
            610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
                660                 665                 670
Leu Gln Gln Pro Gly Ser Ala Arg Ser Thr Arg His Leu Glu Ile Glu
                675                 680                 685
Leu Pro Lys Glu Ala Ser Tyr Gln Glu Gly Asp His Leu Gly Val Ile
            690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Ala Lys Thr Val Ser Val Glu Glu Leu Leu Gln
                740                 745                 750
Tyr Val Glu Leu Gln Asp Pro Val Thr Arg Thr Gln Leu Arg Ala Met
            755                 760                 765
Ala Ala Lys Thr Val Cys Pro Pro His Lys Val Glu Leu Glu Ala Leu
                770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
            820                 825                 830
Ser Ser Ser Pro Arg Val Asp Glu Lys Gln Ala Ser Ile Thr Val Ser
                835                 840                 845
Val Val Ser Gly Glu Ala Trp Ser Gly Tyr Gly Glu Tyr Lys Gly Ile
850                 855                 860
```

-continued

```
Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045

<210> SEQ ID NO 7
<211> LENGTH: 1049
<212> TYPE: PRT
<213> ORGANISM: Bacillus megaterium ATCC 145811
<220> FEATURE:
<223> OTHER INFORMATION: BM3 GVQS

<400> SEQUENCE: 7

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
                20                  25                  30

Ile Ala Asp Glu Leu Gly Glu Ile Phe Lys Phe Glu Ala Pro Gly Arg
            35                  40                  45

Val Thr Arg Tyr Leu Ser Ser Gln Arg Leu Ile Lys Glu Ala Cys Asp
        50                  55                  60

Glu Ser Arg Phe Asp Lys Asn Leu Ser Gln Gly Leu Lys Phe Val Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Val
            115                 120                 125

Gln Lys Trp Glu Arg Leu Asn Ala Asp Glu His Ile Glu Val Pro Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175
```

-continued

```
Ser Met Val Arg Ala Leu Asp Glu Ala Met Asn Lys Gln Gln Arg Ala
            180                 185                 190

Asn Pro Asp Asp Pro Ala Tyr Asp Glu Asn Lys Arg Gln Phe Gln Glu
            195                 200                 205

Asp Ile Lys Val Met Asn Asp Leu Val Asp Lys Ile Ile Ala Asp Arg
210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
            245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
            275                 280                 285

Gln Lys Ala Ala Glu Glu Ala Ala Arg Val Leu Val Asp Pro Val Pro
            290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ser Phe Ser Leu Tyr Ala
            325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Cys Lys Lys Ala Glu Asn Ala His Asn
465                 470                 475                 480

Thr Pro Leu Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
            530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ala Ala
            580                 585                 590
```

-continued

```
Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Gly His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005
```

```
Ala Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045
```

<210> SEQ ID NO 8
<211> LENGTH: 237
<212> TYPE: PRT
<213> ORGANISM: Mesembryanthemum crystallinum
<220> FEATURE:
<223> OTHER INFORMATION: McPfOMT

<400> SEQUENCE: 8

```
Met Asp Phe Ala Val Met Lys Gln Val Lys Asn Thr Gly Leu Leu Gln
1               5                   10                  15

Ser Glu Glu Leu Cys Gln Tyr Ile Leu Arg Thr Ser Val Tyr Pro Arg
                20                  25                  30

Glu Ala Gly Phe Leu Lys Glu Leu Arg Glu Ala Asn Glu Ser His Pro
            35                  40                  45

Asp Ser Tyr Met Ser Thr Ser Pro Leu Ala Gly Gln Leu Met Ser Phe
        50                  55                  60

Val Leu Lys Leu Val Asn Ala Lys Lys Thr Ile Glu Val Gly Val Phe
65                  70                  75                  80

Thr Gly Tyr Ser Leu Leu Leu Thr Ala Leu Ser Ile Pro Asp Asp Gly
                85                  90                  95

Lys Ile Thr Ala Ile Asp Phe Asp Arg Glu Ala Tyr Glu Ile Gly Leu
            100                 105                 110

Pro Phe Ile Arg Lys Ala Gly Val Glu His Lys Ile Asn Phe Ile Glu
        115                 120                 125

Ser Asp Ala Met Leu Ala Leu Asp Asn Leu Leu Gln Gly Gln Glu Ser
    130                 135                 140

Glu Gly Ser Tyr Asp Phe Gly Phe Val Asp Ala Asp Lys Pro Asn Tyr
145                 150                 155                 160

Ile Lys Tyr His Glu Arg Leu Met Lys Leu Val Lys Val Gly Gly Ile
                165                 170                 175

Val Ala Tyr Asp Asn Thr Leu Trp Gly Gly Thr Val Ala Gln Pro Glu
            180                 185                 190

Ser Glu Val Pro Asp Phe Met Lys Glu Asn Arg Glu Ala Val Ile Glu
        195                 200                 205

Leu Asn Lys Leu Leu Ala Ala Asp Pro Arg Ile Glu Ile Val His Leu
    210                 215                 220

Pro Leu Gly Asp Gly Ile Thr Phe Cys Arg Arg Leu Tyr
225                 230                 235
```

<210> SEQ ID NO 9
<211> LENGTH: 363
<212> TYPE: PRT
<213> ORGANISM: Mesembryanthemum crystallinum
<220> FEATURE:
<223> OTHER INFORMATION: AtCOMT

<400> SEQUENCE: 9

```
Met Gly Ser Thr Ala Glu Thr Gln Leu Thr Pro Val Gln Val Thr Asp
1               5                   10                  15

Asp Glu Ala Ala Leu Phe Ala Met Gln Leu Ala Ser Ala Ser Val Leu
                20                  25                  30
```

```
Pro Met Ala Leu Lys Ser Ala Leu Glu Leu Asp Leu Leu Glu Ile Met
         35                  40                  45

Ala Lys Asn Gly Ser Pro Met Ser Pro Thr Glu Ile Ala Ser Lys Leu
 50                  55                  60

Pro Thr Lys Asn Pro Glu Ala Pro Val Met Leu Asp Arg Ile Leu Arg
 65                  70                  75                  80

Leu Leu Thr Ser Tyr Ser Val Leu Thr Cys Ser Asn Arg Lys Leu Ser
                 85                  90                  95

Gly Asp Gly Val Glu Arg Ile Tyr Gly Leu Gly Pro Val Cys Lys Tyr
            100                 105                 110

Leu Thr Lys Asn Glu Asp Gly Val Ser Ile Ala Ala Leu Cys Leu Met
        115                 120                 125

Asn Gln Asp Lys Val Leu Met Glu Ser Trp Tyr His Leu Lys Asp Ala
    130                 135                 140

Ile Leu Asp Gly Gly Ile Pro Phe Asn Lys Ala Tyr Gly Met Ser Ala
145                 150                 155                 160

Phe Glu Tyr His Gly Thr Asp Pro Arg Phe Asn Lys Val Phe Asn Asn
                165                 170                 175

Gly Met Ser Asn His Ser Thr Ile Thr Met Lys Lys Ile Leu Glu Thr
            180                 185                 190

Tyr Lys Gly Phe Glu Gly Leu Thr Ser Leu Val Asp Val Gly Gly Gly
        195                 200                 205

Ile Gly Ala Thr Leu Lys Met Ile Val Ser Lys Tyr Pro Asn Leu Lys
    210                 215                 220

Gly Ile Asn Phe Asp Leu Pro His Val Ile Glu Asp Ala Pro Ser His
225                 230                 235                 240

Pro Gly Ile Glu His Val Gly Gly Asp Met Phe Val Ser Val Pro Lys
                245                 250                 255

Gly Asp Ala Ile Phe Met Lys Trp Ile Cys His Asp Trp Ser Asp Glu
            260                 265                 270

His Cys Val Lys Phe Leu Lys Asn Cys Tyr Glu Ser Leu Pro Glu Asp
        275                 280                 285

Gly Lys Val Ile Leu Ala Glu Cys Ile Leu Pro Glu Thr Pro Asp Ser
    290                 295                 300

Ser Leu Ser Thr Lys Gln Val Val His Val Asp Cys Ile Met Leu Ala
305                 310                 315                 320

His Asn Pro Gly Gly Lys Glu Arg Thr Glu Lys Glu Phe Glu Ala Leu
                325                 330                 335

Ala Lys Ala Ser Gly Phe Lys Gly Ile Lys Val Val Cys Asp Ala Phe
            340                 345                 350

Gly Val Asn Leu Ile Glu Leu Leu Lys Lys Leu
        355                 360

<210> SEQ ID NO 10
<211> LENGTH: 232
<212> TYPE: PRT
<213> ORGANISM: Mesembryanthemum crystallinum
<220> FEATURE:
<223> OTHER INFORMATION: AOMT

<400> SEQUENCE: 10

Met Ala Lys Asp Glu Ala Lys Gly Leu Leu Lys Ser Glu Glu Leu Tyr
 1               5                  10                  15

Lys Tyr Ile Leu Glu Thr Ser Val Tyr Pro Arg Glu Pro Glu Val Leu
             20                  25                  30
```

-continued

```
Arg Glu Leu Arg Asn Ile Thr His Asn His Pro Gln Ala Gly Met Ala
             35                  40                  45
Thr Ala Pro Asp Ala Gly Gln Leu Met Gly Met Leu Leu Asn Leu Val
 50                  55                  60
Asn Ala Arg Lys Thr Ile Glu Val Gly Val Phe Thr Gly Tyr Ser Leu
 65                  70                  75                  80
Leu Leu Thr Ala Leu Thr Leu Pro Glu Asp Gly Lys Val Ile Ala Ile
                 85                  90                  95
Asp Met Asn Arg Asp Ser Tyr Glu Ile Gly Leu Pro Val Ile Lys Lys
            100                 105                 110
Ala Gly Val Glu His Lys Ile Asp Phe Lys Glu Ser Glu Ala Leu Pro
            115                 120                 125
Ala Leu Asp Glu Leu Leu Asn Asn Lys Val Asn Glu Gly Gly Phe Asp
            130                 135                 140
Phe Ala Phe Val Asp Ala Asp Lys Leu Asn Tyr Trp Asn Tyr His Glu
145                 150                 155                 160
Arg Leu Ile Arg Leu Ile Lys Val Gly Gly Ile Ile Val Tyr Asp Asn
                165                 170                 175
Thr Leu Trp Gly Gly Ser Val Ala Glu Pro Asp Ser Ser Thr Pro Glu
            180                 185                 190
Trp Arg Ile Glu Val Lys Lys Ala Thr Leu Glu Leu Asn Lys Lys Leu
            195                 200                 205
Ser Ala Asp Gln Arg Val Gln Ile Ser Gln Ala Ala Leu Gly Asp Gly
            210                 215                 220
Ile Thr Ile Cys Arg Arg Leu Tyr
225                 230
```

<210> SEQ ID NO 11
<211> LENGTH: 43
<212> TYPE: DNA
<213> ORGANISM: Bacillus megaterium
<220> FEATURE:
<223> OTHER INFORMATION: Primer sequence

<400> SEQUENCE: 11
ttgataaaaa cttaagtcaa ggtcttaaat tgtacgtga ttt        43

<210> SEQ ID NO 12
<211> LENGTH: 43
<212> TYPE: DNA
<213> ORGANISM: Bacillus megaterium
<220> FEATURE:
<223> OTHER INFORMATION: Primer sequence

<400> SEQUENCE: 12
aaatcacgta caaatttaag accttgactt aagttttat caa        43

<210> SEQ ID NO 13
<211> LENGTH: 43
<212> TYPE: DNA
<213> ORGANISM: Bacillus megaterium
<220> FEATURE:
<223> OTHER INFORMATION: Primer sequence

<400> SEQUENCE: 13
tggatgaagc aatgaacaag cagcagcgag caaatccaga cga        43

<210> SEQ ID NO 14
<211> LENGTH: 43
<212> TYPE: DNA

```
<213> ORGANISM: Bacillus megaterium
<220> FEATURE:
<223> OTHER INFORMATION: Primer sequence

<400> SEQUENCE: 14
tcgtctggat tgctcgctg ctgcttgttc attgcttcat cca                43

<210> SEQ ID NO 15
<211> LENGTH: 30
<212> TYPE: DNA
<213> ORGANISM: Bacillus megaterium
<220> FEATURE:
<223> OTHER INFORMATION: Primer sequence

<400> SEQUENCE: 15
tatggccaac tgctccttcg ttttccctat                              30

<210> SEQ ID NO 16
<211> LENGTH: 30
<212> TYPE: DNA
<213> ORGANISM: Bacillus megaterium
<220> FEATURE:
<223> OTHER INFORMATION: Primer sequence

<400> SEQUENCE: 16
atagggaaaa cgaaggagca gttggccata                              30
```